United States Patent [19]

Battaglia et al.

[11] 4,199,412
[45] Apr. 22, 1980

[54] HALIDE ION-SELECTIVE DEVICES AND METHOD

[75] Inventors: Charles J. Battaglia, Rochester; Denise S. Secord, Webster; Sang H. Kim, Rochester, all of N.Y.

[73] Assignee: Eastman Kodak Company, Rochester, N.Y.

[21] Appl. No.: 956,527

[22] Filed: Oct. 31, 1978

[51] Int. Cl.$^2$ ............................................. G01N 27/46
[52] U.S. Cl. ................................. 204/1 T; 204/195 P; 204/195 B
[58] Field of Search ............... 204/1 B, 195 P, 195 B, 204/195 F; 128/2 E; 324/29, 30 R

[56] References Cited

U.S. PATENT DOCUMENTS

| | | | |
|---|---|---|---|
| 3,591,482 | 7/1971 | Neff et al. | 204/195 F |
| 3,694,163 | 9/1972 | Sherelis | 23/253 TP |
| 3,856,649 | 12/1974 | Genshaw et al. | 204/195 F |
| 3,912,614 | 10/1975 | Spracklen et al. | 204/195 B |
| 3,979,274 | 9/1976 | Newman | 204/195 B |
| 4,053,381 | 10/1977 | Hamblen et al. | 204/195 M |
| 4,115,209 | 9/1978 | Freiser et al. | 204/1 T |

OTHER PUBLICATIONS

R. P. Buck, Proc. Analyt. Div. Chem. Soc., pp. 332–334, Nov. 1977.
Research Disclosure, No. 16113, pp. 29–39, Sep. 1977.
Research Disclosure, No. 15767, pp. 61–66, May 1977.

Primary Examiner—G. L. Kaplan
Attorney, Agent, or Firm—Arthur H. Rosenstein

[57] ABSTRACT

Halide ion-sensitive devices and methods for their use are described. The devices contain a halide ion-permeable overlayer which is superposed on a layer of silver halide and meets certain criteria of thickness and permeability and/or certain compositional criteria. The methods involve bringing a portion of a solution to be analyzed into contact with the halide ion-permeable overlayer and, within a selected time thereafter, measuring the difference in potential between the portion of solution and the silver halide layer.

39 Claims, 3 Drawing Figures

HALIDE ION-SELECTIVE DEVICES AND METHOD

BACKGROUND OF THE INVENTION

1. Field of the Invention

The present invention relates to halide ion-sensitive devices, and particularly to halide ion-sensitive devices such as electrodes which can be used to determine the concentration of certain halide ions in a solution in a short period of time without significant interference from other halide ions or other materials, such as uric acid, which may also be present in the solution.

2. Description Relative to the Prior Art

Ion-sensitive electrodes comprising a layer of silver in electrochemical contact with a layer of silver halide (especially silver chloride) are well known. Descriptions of silver/silver chloride electrodes may be found, for example, in U.S. Pat. Nos. 3,883,495; 3,502,560; 3,591,482; and 3,856,649, and in *Research Disclosure* No. 16113, Volume 161, September, 1977.

Such electrodes can be useful as reference electrodes and also as sensing electrodes for detecting chloride ions in aqueous solutions. However, in measuring chloride ion activity with a silver/silver chloride electrode in order to determine chloride ion concentration in a solution, significant errors or bias in the determination can result due to the presence in the solution of other materials, such as bromide ions or uric acid, which may come into contact with the electrode.

U.S. Pat. No. 3,591,482 describes a silver/silver chloride electrode which is overcoated with a layer of alkyl methacrylate to protect the electrode from physical damage and corrosion, while permitting passage of chloride ions.

R. P. Buck, "Virtues and Limitations of ISE for Measurements in Biological Systems", plenary lecture, *Proc. Analyt. Div. Chem. Soc.*, November, 1977, pages 332 through 334, discusses ion-selective electrodes containing various surface coatings. The particular overcoats described herein are not disclosed.

U.S. Pat. No. 3,979,274 recognizes that an enzyme electrode, such as a platinum electrode, which measures hydrogen peroxide activity, can encounter interference from substances such as uric acid or other low molecular weight materials. It describes a laminated overcoat comprising two layers bonded together by an enzyme preparation to permit passage of hydrogen peroxide but prevent passage of other materials. One of the layers may comprise a cellulose ester, silicone rubber, or methyl methacrylate. No suggestion is made that such overcoats would serve any useful purpose on halide ion-sensitive electrodes.

U.S. Pat. No. 3,694,163 describes an enzyme electrode overcoated with a phase-inverted cellulose ester material containing a reagent and an amide swelling agent. It is not suggested that such a layer could be used with a halide ion-sensitive electrode, or would have any effect on possible interferents.

U.S. Pat. No. 3,912,614 describes a noble metal electrode coated with a membrane comprising polyhydroxyl ethyl methacrylate to allow passage of oxygen, but prevent diffusion of other materials. The membrane must be 100 to 500 microns thick, according to this patent. Such a membrane, to accomplish its purpose, will necessarily result in long response times in making each measurement; i.e., the thicker the membrane, the longer the time required to make an accurate measurement after the sensing device is brought into contact with the solution under investigation.

Long response times are particularly undesirable in situations where numerous analyses must be made each day, or where numerous analyses are intended to be made by an automated or semi-automated assembly-line type analytical method.

Accordingly, it would be desirable to provide a sensing device for the detection of halide ions in solution which utilizes an overlayer to prevent interference by other materials, but wherein the overlayer is relatively thin (e.g., 1 to 8 microns), so that an accurate analysis could be carried out within a relatively short period of time (e.g., within 5 minutes) after the device is brought into contact with the solution to be analyzed.

SUMMARY OF THE INVENTION

The present invention provides a halide ion-sensitive device which is substantially free from interference by low molecular weight species, such as $Br^\ominus$, uric acid, etc, and methods for their use, such electrodes having the desirable capabilities noted above; i.e., determinations of halide ion concentration (e.g., chloride concentration) in solutions such as blood serum can be made, for example, within 5 minutes after contacting such a device with a portion of such a solution.

Such a device can include means for making potentiometric measurements related to halide ion concentrations, such as an electrode comprising a support having a silver layer superposed thereon. The silver layer is in electrochemical contact with a layer of silver halide (e.g., silver chloride) having superposed thereon a halide ion-permeable overlayer.

The halide ion-permeable overlayer employed in the invention must meet certain diffusion coefficient and permeability parameters that vary according to the desired thickness of the overlayer. For example, as the layer thickness increases, the diffusion coefficient increases, and as the layer thickness decreases, the permeability decreases. In one preferred embodiment, there is provided a halide ion-permeable overlayer which is from about 1 to about 8 microns thick, has a diffusion coefficient of at least $2.5 \times 10^{-10}$ cm$^2$/sec with respect to the halide ions to be detected, and has a permeability of less than $2 \times 10^{-8}$ cm$^2$/sec to materials which could interfere with the accurate determination of halide ion concentration.

In accordance with a particularly preferred embodiment, specific halide ion-permeable overlayer compositions are provided, as described in further detail hereinafter.

Alternatively, a device provided by the present invention includes an n- and p-type silicon support having a silicon dioxide layer superposed thereon. The silicon dioxide layer is in electrochemical contact with a layer of silver halide (e.g., silver chloride) having the halide ion-permeable overlayer superposed thereon.

The present invention also provides methods for determining halide ion concentration in solution. These methods involve bringing a portion of the solution into contact with the halide ion-permeable overlayer of either of the devices described above and, within a selected period of time, usually within 5 minutes thereafter, measuring the difference in potential between the portion of solution and the silver halide layer.

DESCRIPTION OF THE PREFERRED EMBODIMENTS

Ag/AgCl electrodes of a variety of formats, compositions and constructions are well known in the art, and their preparation is well documented in numerous patents discussed hereinabove in the Background of the Invention. Of particular interest are those Ag/AgCl electrodes prepared in the manner and according to the format described in aforementioned *Research Disclosure* Volume 161.

Electrode elements of this type can be prepared using a number of well-known techniques which include, by way of example, dipping a layer of silver such as a wire, foil or supported thin layer of silver into a solution of molten silver halide. According to a preferred embodiment, the silver-silver halide electrode is produced by vacuum-depositing silver onto a suitable support, preferably an insulating polymeric film, and then chemically converting a surface stratum of the silver layer to silver halide. Generally, techniques for chemically converting metal to metal halide involve exposure or contact of the surface of the metal, in this case silver, with a solution of a salt of the halide to be formed for a period and at a temperature sufficient to cause the desired conversion. Typical conditions for this sort of chemical conversion are well known, and examples of simple and preferred techniques may be found in aforementioned *Research Disclosure* Volume 161. Other useful techniques for preparing such electrodes are described in U.S. Pat. Nos. 3,591,482 to Neff et al, issued July 6, 1971; 3,502,560 to Wise, issued Mar. 24, 1970; and 3,806,439 to Light et al, issued Apr. 23, 1974. Although the teachings of all of these references are directed primarily to the preparation of wire electrodes, the electrodes described herein may also be constructed on thin films of polymeric support, as described in the aforementioned *Research Disclosure* Volume 161. Alternatively, a discrete layer of silver chloride may be coated over the silver layer, so long as appropriate electrochemical contact between the silver and the silver chloride is achieved.

Although it is possible to obtain the silver-silver salt interface with substantially any ratio of silver layer to salt layer thickness, in a preferred embodiment which assures a sufficiently dense layer of silver salt, the salt layer has a thickness equal to at least 10 percent of the overall thickness of the silver layer. According to an especially preferred embodiment, from about 10 to about 20 percent of the thickness of the silver layer is converted to silver chloride using chemical conversion techniques.

Preferred halide ion-permeable overlayers of the present invention having a thickness (dry thickness) of from about 1 to about 8 microns have a diffusion coefficient of at least $2.5 \times 10^{-10}$ cm$^2$/sec with respect to the halide ions to be detected and a permeability of less than $2 \times 10^{-8}$ cm$^2$/sec to materials which could interfere with the accurate determination of halide ion concentration. These properties are determined by known techniques, such as radio tracers, conductivity, ion-selective electrodes, etc.

Preferred halide ion-permeable overlayer compositions of the invention are selected from:

(a) cellulose esters;
(b) polymers derived from 45 weight percent to 100 weight percent of one or a mixture of monomers selected from the group consisting of:
  (1) acrylic acids;
  (2) methacrylic acids;
  (3) acrylamides;
  (4) alkylacrylamides wherein the alkyl portion has from 1 to 5 carbon atoms;
  (5) hydroxyalkyl acrylates wherein the alkyl portion has from 1 to 5 carbon atoms; and
  (6) hydroxyalkyl methacrylates wherein the alkyl portion has from 1 to 5 carbon atoms; and
(c) mixtures of gelatin, silver halide/gelatin emulsion, and an acid.

Some specific examples of preferred compositions which meet the preferred diffusion and permeability criteria for a halide ion-permeable overlayer of the invention include:

(a) cellulose acetate having from about 36.5 weight percent to about 40.0 weight percent acetyl content;
(b) poly(acrylamide-co-methacrylic acid) (weight ratio: 45/55);
(c) poly(methylacrylamide-co-methacrylic acid) (weight ratio: 50/50);
(d) poly(methacrylamide-co-2-hydroxyethyl-methacrylate-co-methacrylic acid-co-2-acetoacetoxyethylmethacrylate) (weight ratio: 28/28/34/10);
(e) poly(methacrylic acid);
(f) poly(acrylic acid); and
(g) poly(2-hydroxyethylacrylate).

The thickness of the overlayer should preferably be from about 1 to about 8 microns. Thicknesses can vary depending upon the particular composition chosen and/or the necessity of meeting specific diffusion and permeability criteria.

For example, a useful composition for an overlayer of the present invention is cellulose acetate. In order to meet the preferred diffusion and permeability criteria described above, preferred cellulose acetates should have from about 36.5 percent to about 40.0 percent acetyl content by weight and the thickness of the overlayer should be from about 7.6 to about 1.3 microns, depending upon the percent acetyl content. An empirical formula for determining the preferred thickness in microns of a cellulose acetate overlayer, depending upon its acetyl content, is: preferred thickness = $73.3 - (1.8) \times$ (percent acetyl content). An advantage of these preferred cellulose acetates is that they are capable of rapidly carrying out detection of halide ions, e.g., within 5 minutes or less.

Figure 1:
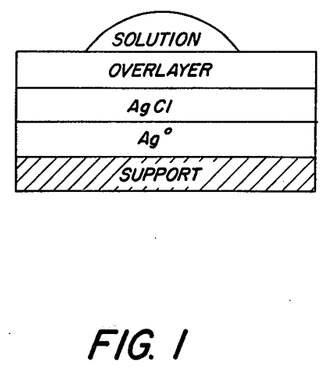
FIG. 1 is a non-scale representation of a potentiometric device in accordance with one embodiment of the present invention.

The specific method of application of the overlayers of the present invention is, of course, largely dependent upon the physical shape of the underlying Ag/AgCl or other electrode. Thus, when the Ag/AgCl electrode is a wire electrode, the simplest method for applying the overlayer may be dipping or spraying. When the underlying electrode is in a planar format, illustrated in FIG. 1 of the drawings and described in *Research Disclosure*, Volume 161 referred to above, it is advantageous to coat the overlayer according to techniques well known to those skilled in the coating art, although other techniques, such as laminating, can be used, also.

When using a coating mode of application, the overlayer is generally applied by forming a solution of the constituent composition in a suitable solvent, applying the solution to the electrode, and then driving off the solvent under drying conditions.

Useful solvents for water-insoluble polymers, such as cellulose acetates, include acetone, methyl ethyl ketone, methyl acetate, acetone mixtures of methanol, 2-ethoxy ethanol, or diacetone alcohol, and dichloromethane:methanol (90:10 by weight).

Surfactants may also be included in the solutions as appropriate to achieve good coating characteristics, such as TX-100.

Figure 2:
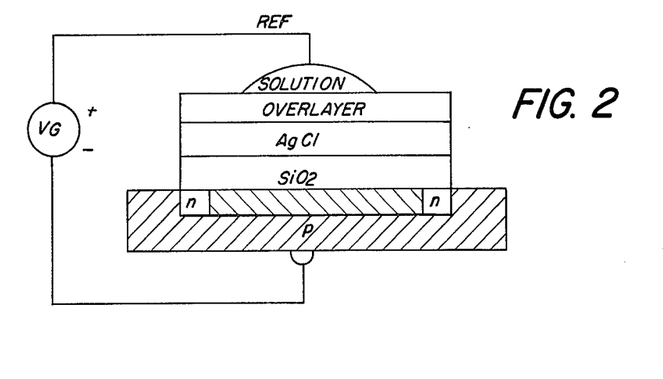
FIG. 2 is a non-scale representation of a potentiometric device in accordance with an alternative embodiment of the present invention.

A silver halide layer may also be vacuum deposited on a semiconductor substrate, such as silicon dioxide/silicon to prepare a field effect potentiometric device. Overlayers of the type described in this application are useful for application to so-called ISFET's, i.e., ion-selective field effect transistors sensitive to chloride or bromide ion, as described by Bergveld (P. Bergveld, IEEE Trans., Biomed., Eng., 17, 70 [1970], and P. Bergveld, IEEE Trans., Biomed., Eng., 19, 342 [1972]), and R. P. Buck et al, *Analytical Chemistry*, Volume 49, No. 14, December, 1977, page 2315. As illustrated in FIG. 2 of the drawings, such FET's, in the case of bromide- or chloride-selective transistors, can comprise a layer of an insoluble salt, such as silver bromide or silver chloride coated over a silicon dioxide layer to form a gate in contact with a silicon surface appropriately doped to define a p or n channel upon application of a sample under test to the silver halide layer.

The halide ion-permeable overlayers described herein are coated over the silver halide layers to inhibit the effect of interfering ions which may be present in the solution under assay. Particularly, the halide ion-permeable overlayers of the invention reduce interference in determinations of concentration of particular halide ions. Interference from other halides (e.g., from bromide when chloride is being measured, etc.), as well as interference from uric acid, sulfur- and nitrogen-containing compounds, other low molecular weight compounds, and large molecules, such as proteins, can be significantly reduced or completely eliminated by use of such overlayers.

The overlayers also provide physical protection against abrasion of fragile silver halide layers.

The following examples are presented to further illustrate the preparation and performance of some preferred embodiments of the invention.

In the Examples, planar, dry-operative Ag/AgCl electrodes were prepared as described in the aforementioned *Research Disclosure*, Volume 161, and then overcoated with various halide ion-permeable overlayer compositions from a solvent, in some cases containing a small amount of a surfactant, such as Triton X-100 (commercially available from Rohm and Haas Company).

Performance testing was done in both differential and absolute modes.

In the differential mode, matched Ag/AgCl electrodes were tested using fiber bridges which connect reference and test solutions, as described in *Research Disclosure* No. 15767, Volume 157, May, 1977. Test solutions comprised stock human blood serum pools spiked with NaBr at 0.1 or 0.5 mM or uric acid at 1.0 mM. The measured potential difference between spiked and unspiked human serum ($\Delta$emf) was taken as a measure of the bias in mV and expressed as percent bias, which equals $\Delta$emf times [−4], assuming a consistent Nernstian response. A three-minute time was chosen as the endpoint.

In the absolute mode, the overcoated Ag/AgCl electrodes were tested by direct potentiometry in a cell without transference using a Beckman sodium ion-sensitive glass electrode or a microreference electrode, MI-410 (Microelectrodes, Inc.), as the reference. Test solutions comprised stock human blood serum pools spiked with either KBr at 0.5 mM or uric acid at 0.6 mM (10 mg/dl). The difference in measured potential between spiked and unspiked human serum ($\Delta$emf) was taken as a measure of the bias in mV. The response time of the electrode was chosen as that time at which the potential reached a steady state, i.e., drifted at a constant rate.

All tests were performed at ambient conditions (35 to 50 percent RH; 21° to 23° C.), unless otherwise stated.

EXAMPLE 1

Effectiveness of Various Overlayer Compositions in Reducing $Br^\ominus$ and Uric Acid Interferences A series of chloride ion-sensitive electrodes were prepared as described above, each having an overlayer comprising a different composition, except for the control, which contained no overlayer. The electrodes were then tested in the differential mode with spiked and unspiked human blood serum pools, as described above. Measurements were made 3 minutes after the serum solution contacted the overlayer. The results, as shown in Table I, indicate that all of the overlayer compositions tested reduce interference by bromide and uric acid. Cellulose acetate (having from 36.5 percent to 40.0 percent acetyl content) was the most effective in this respect.

TABLE I

| Composition of Electrode Overlayer | Thickness of Overlayer (microns) | Bias (percent) 0.5 mM $Br^\ominus$ | 1.0 mM Uric Acid |
|---|---|---|---|
| Bare control electrode (no overlayer) | 0 | 25 | 8 |
| poly(2-hydroxyethylacrylate) | 7.5 | 21 | 2 |
| poly(acrylic acid) | 2.5 | 17 | 2 |
| poly(methacrylic acid) | 2.5 | 12 | 1 |
| poly(methacrylamide-co-2-hydroxyethylmethacrylate-co-methacrylic acid-co-2-acetoacetoxyethylmethacrylate) (28/28/34/10) | 5 | 12 | <1 |
| poly(methacrylamide-co-methacrylic acid) (50/50) | 5 | 10 | <1 |
| poly(acrylamide-co-methacrylic acid) (45/55) | 5 | 6 | 1 |
| Cellulose acetate (36.5 percent - 40 percent acetyl) | 1-8 | <1-5 | <1 |

Various polymeric overlayers that do not meet the diffusion and permeability criteria described above have been likewise treated, and no significant reduction in bias was found. These include vinyl acetate, poly(acrylamido-co-2-acetoacetoxyethyl methacrylate) (90:10), agarose, cellulose nitrate, polyvinyl alcohol and poly(vinyl pyrrolidone).

EXAMPLE 2

Effectiveness of Gel/AgCl/Acid Overlayer in Reducing $Br^\ominus$ and Uric Acid Interferences Two electrodes were prepared as in Example 1, one being a bare control without an overlayer, and the other having an overlayer comprising a mixture of:

(1) 5 g/m$^2$ of deionized gelatin hardened with 0.075 g/m$^2$ of bis(vinylsulfonylmethyl)ether;

(2) 5 g/m$^2$ of AgCl emulsion comprising a 1:1 mix of AgCl having a grain size of 0.15 to 0.6 micron at pAg 4 to 5.6 and gelatin;

(3) 7.5 mM/m$^2$ of potassium acid phthalate (potassium dihydrogen phosphate or nitric acid can also be used); and (4) 0.025 g/m$^2$ of Triton X-100 surfactant.

This mixture was coated from solution at pH 4.7. Differential mode testing of the two electrodes was carried out in spiked and unspiked human blood serum pools, as described above. The results shown in Table II indicate that the gel/AgCl/Acid overlayer causes some reduction of $Br^\ominus$ interference and significant reduction of uric acid interference.

TABLE II

| Composition of Electrode Overlayer | Bias (percent) | |
|---|---|---|
| | 0.1 mM $Br^\ominus$ | 1.0 mM Uric Acid |
| Bare control | 8 | 10 |
| gel/AgCl/Acid | 3 | 0 |

EXAMPLE 3

Effect of Thickness and Acetyl Content of Cellulose Acetate Overlayers

A series of chloride ion-sensitive electrodes were prepared as described above, with overlayers of cellulose acetate of varying thickness and acetyl content coated from acetone. An uncoated electrode was also prepared to serve as a control. The electrodes were tested in the absolute mode with spiked and unspiked human blood serum pools, as described above. The response time of the electrode was chosen as that time at which the potential reached a steady state, i.e., drifted at a constant rate. The results, shown in Table III, illustrate that acetyl content and thickness are interrelated in respect to achieving a desirable combination of response time and interference reduction with cellulose acetate overlayers.

EXAMPLE 4

Comparison of Permeability of $Cl^\ominus$ and $Br^\ominus$ Through Cellulose and Cellulose Acetate Layers The permeability of chloride and bromide ions through layers of cellulose and cellulose acetate (37.6 percent acetyl) was determined by placing the halide ion in one compartment of a concentration cell and water in the second, with the compartments separated by the layer being tested. The resulting data in Table IV shows that cellulose does not meet the permeability criteria for an overlayer useful according to the invention to reduce bromide interference with a chloride ion-sensitive device, while cellulose acetate (37.6 percent acetyl) does meet the criteria.

TABLE IV

| | Permeability in cm$^2$/sec | |
|---|---|---|
| Overlayer Composition | to $Cl^\ominus$ | to $Br^\ominus$ |
| cellulose (20 g/m$^2$) | $9.2 \times 10^{-7}$ | $7.0 \times 10^{-7}$ |
| cellulose acetate (5 g/m$^2$) (37.6 percent acetyl) | $3 \times 10^{-9}$ | $6 \times 10^{-9}$ |

EXAMPLE 5

Figure 3:
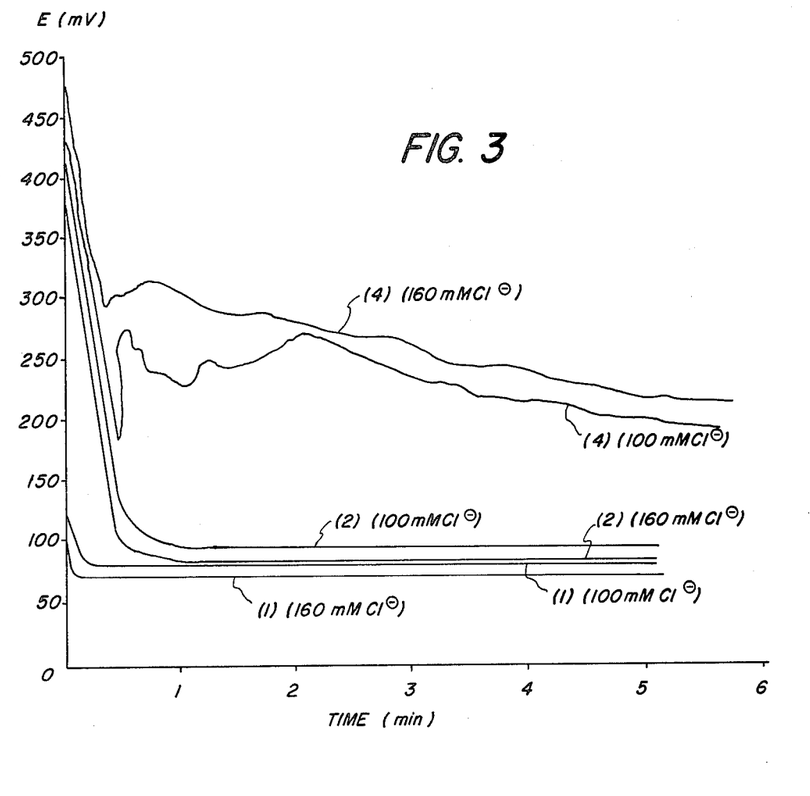
FIG. 3 is a comparative graphic representation of the potential versus time performances of an embodiment of the present invention and some of those suggested by the prior art.

Comparison of Overlayers Comprising Methyl Methacrylate and Cellulose Acetate In this example, an Ag/AgCl electrode (2) coated with an overlayer according to the present invention (cellulose acetate-39.5 percent acetyl-3 microns thick) was compared with a similar electrode (3) coated with an overlayer described in Neff, U.S. Pat. No. 3,591,482 (methyl methacrylate-25 microns thick). A 6.3-micron thick electrode overlayer (4) (within the thickness range prescribed by the present invention) of methyl methacrylate was also tested. An uncoated Ag/AgCl electrode (1) served as the control. The electrodes were prepared as described previously and tested in solutions containing 100 and 160 mM $Cl^\ominus$, using the MI-401 as the reference electrode.

Plots of potential versus time for each electrode in each solution are shown in FIG. 3 of the drawings. The potential for electrode (3) remained too high to be plotted within the time allowed, indicating an insufficient response time (>5 minutes). The response of electrode (4), though measurable, was too erratic during the time allowed to be of any use. Also, the plot of electrode (4) showed higher potential for a 160 mM $Cl^\ominus$ solution than for a 100 mM $Cl^\ominus$ solution within the time allowed, which is the reverse of the correct relationship, as shown by the plots for electrodes (1) and (2). The

TABLE III

| Percent Acetyl In Cellulose Acetate Overlayer | Overlayer Thickness (microns) | Response Time (minutes) | Bias (mV) | |
|---|---|---|---|---|
| | | | 0.5 mM $Br^\ominus$ | 10 mg/dl Uric Acid |
| Bare control (no overlayer) | 0 | <1 | 7.5 | 1.5 |
| 40.0 | 5 | 8** | <1 | * |
| 40.0 | 1.25 | 2 | <1 | * |
| 40.0 (control A) | 0.125 | <2 | 8 | * |
| 39.8 | 5 | 10** | <1 | <1 |
| 39.4 | 5 | 5–10** | <1 | <1 |
| 39.4 | 1.25 | 1–2 | <1 | <1 |
| 38.8 | 5 | 1–2 | <1 | <1 |
| 37.6 | 5 | <1 | <1 | <1 |
| 37.6 | 1.25 | <1 | 3.5 | 0 |

*Not tested
**Response times are not desireable, although interference is inhibited plots for electrode (4) eventually crossed over each other at a time greater than 10 minutes (not shown).

These results indicate that an overlayer of methyl methacrylate, as taught by Neff, is not useful in the practice of the present invention.

The invention has been described in detail with particular reference to preferred embodiments thereof, but it will be understood that variations and modifications can be effected within the spirit and scope of the invention.

What is claimed is:

1. In a potentiometric device for the detection of halide ions in a solution, said device comprising: (1) a layer of silver halide in electrochemical contact with means for making potentiometric measurements related to halide ion concentration, and (2) a halide ion-permeable overlayer superposed on said layer of silver halide,
    the improvement wherein said halide ion-permeable overlayer consists essentially of a composition that:
    (a) is from about 1 to about 8 microns thick;
    (b) has a diffusion coefficient of at least $2.5 \times 10^{-10}$ cm$^2$/sec with respect to the halide ions to be detected; and
    (c) has a permeability of less than $2 \times 10^{-8}$ cm$^2$/sec to materials which could interfere with said detection of halide ions;
whereby said halide ion-permeable overlayer is capable of inhibiting interference due to the presence of one or more of said interfering materials in said solution, and said potentiometric device is capable of accurately carrying out said detection of halide ions within 5 minutes after a portion of said solution is brought into contact with said halide ion-permeable overlayer.

2. The device of claim 1 wherein said halide ions are chloride ions and said silver halide is silver chloride.

3. The device of claim 1 wherein said halide ion-permeable overlayer contains a surfactant.

4. The device of claim 1 wherein said means for making potentiometric measurements comprises a doped silicon support having a silicon dioxide layer superposed thereon.

5. In a potentiometric device for the detection of halide ions in a solution, said device comprising: (1) a layer of silver halide in electrochemical contact with means for making potentiometric measurements related to halide ion concentration, and (2) a halide ion-permeable overlayer superposed on said layer of silver halide, the improvement wherein said halide ion-permeable overlayer is from about 1 to about 8 microns thick and consists essentially of a composition selected from the group consisting of:
    (a) cellulose esters having from about 36.5 weight percent to about 40.0 weight percent acetyl content;
    (b) polymers derived from 45 weight percent to 100 weight percent of monomers selected from the group consisting of:
        (1) acrylic acids;
        (2) methacrylic acids;
        (3) acrylamides;
        (4) alkylacrylamides wherein the alkyl portion has from 1 to 5 carbon atoms;
        (5) hydroxyalkyl acrylates wherein the alkyl portion has from 1 to 5 carbon atoms; and
        (6) hydroxyalkyl methacrylates wherein the alkyl portion has from 1 to 5 carbon atoms; and
    (c) mixtures of gelatin, silver halide/gelatin emulsion and an acid.

6. The device of claim 5 wherein said halide ion-permeable overlayer consists essentially of a composition selected from the group consisting of:
    (a) cellulose acetate having from about 36.5 weight percent to about 40.0 weight percent acetyl content;
    (b) poly(acrylamide-co-methacrylic acid) (weight ratio: 45/55);
    (c) poly(methacrylamide-co-methacrylic acid) (weight ratio: 50/50);
    (d) poly(methacrylamide-co-2-hydroxyethylmethacrylate-co-methacrylic acid-co-2-acetoacetoxyethylmethacrylate) (weight ratio: 28/28/34/10);
    (e) poly(methacrylic acid);
    (f) poly(acrylic acid); and
    (g) poly(2-hydroxyethylacrylate).

7. In a potentiometric device for the detection of halide ions in a solution, said device comprising: (1) a layer of silver halide in electrochemical contact with means for making potentiometric measurements related to halide ion concentration, and (2) a halide ion-permeable overlayer superposed on said layer of silver halide,
    the improvement wherein said halide ion-permeable overlayer is from about 1 to about 8 microns thick and consists essentially of cellulose acetate having from about 36.5 weight percent to about 40.0 weight percent acetyl content.

8. The device of claim 7 wherein said halide ions are chloride ions and said silver halide is silver chloride.

9. The device of claim 7 wherein said halide ion-permeable overlayer contains a surfactant.

10. The device of claim 7 wherein said means for making potentiometric measurements comprises a doped silicon support having a silicon dioxide layer superposed thereon.

11. In a halide ion-sensitive electrode for the detection of halide ions in a solution, said electrode comprising: (1) a layer of silver halide superposed on and in electrochemical contact with a layer of silver, and (2) a halide ion-permeable overlayer superposed on said layer of silver halide,
    the improvement wherein said halide ion-permeable overlayer consists essentially of a composition that:
    (a) is from about 1 to about 8 microns thick;
    (b) has a diffusion coefficient of at least $2.5 \times 10^{-10}$ cm$^2$/sec with respect to the halide ions to be detected; and
    (c) has a permeability of less than $2 \times 10^{-8}$ cm$^2$/sec to materials which could interfere with said detection of halide ions;
whereby said halide ion-permeable overlayer is capable of inhibiting interference due to the presence of one or more of said interfering materials in said solution, and said halide ion-sensitive electrode is capable of accurately carrying out said detection of halide ions within 5 minutes after a portion of said solution is brought into contact with said halide ion-permeable overlayer.

12. The electrode of claim 11 wherein said halide ions are chloride ions and said silver halide is silver chloride.

13. The electrode of claim 11 wherein said halide ion-permeable overlayer contains a surfactant.

14. In a halide ion-sensitive electrode for the detection of halide ions in a solution, said electrode comprising: (1) a layer of silver halide superposed on and in electrochemical contact with a layer of silver, and (2) a halide ion-permeable overlayer superposed on said layer of silver halide, the improvement wherein said halide ion-permeable overlayer is from about 1 to about 8 microns thick and consists essentially of a composition selected from the group consisting of:
  (a) cellulose esters having from about 36.5 weight percent to about 40.0 weight percent acetyl content;
  (b) polymers derived from 45 weight percent to 100 weight percent of one or a mixture of monomers selected from the group consisting of:
    (1) acrylic acids;
    (2) methacrylic acids;
    (3) acrylamides;
    (4) alkylacrylamides wherein the alkyl portion has from 1 to 5 carbon atoms;
    (5) hydroxyalkyl acrylates wherein the alkyl portion has from 1 to 5 carbon atoms; and
    (6) hydroxyalkyl methacrylates wherein the alkyl portion has from 1 to 5 carbon atoms; and
  (c) mixtures of gelatin, silver halide/gelatin emulsion and an acid.

15. The electrode of claim 14 wherein said halide ion-permeable overlayer consists essentially of a composition selected from the group consisting of:
  (a) cellulose acetate having from about 36.5 weight percent to about 40.0 weight percent acetyl content;
  (b) poly(acrylamide-co-methacrylic acid) (weight ratio: 45/55);
  (c) poly(methacrylamide-co-methacrylic acid) (weight ratio: 50/50);
  (d) poly(methacrylamide-co-2-hydroxyethylmethacrylate-co-methacrylic acid-co-2-acetoacetoxyethylmethacrylate) (weight ratio: 28/28/34/10);
  (e) poly(methacrylic acid);
  (f) poly(acrylic acid); and
  (g) poly(2-hydroxyethylacrylate).

16. In a halide ion-sensitive electrode for the detection of halide ions in a solution, said electrode comprising: (1) a layer of silver halide superposed on and in electrochemical contact with a layer of silver, and (2) a halide ion-permeable overlayer superposed on said layer of silver halide,
  the improvement wherein said halide ion-permeable overlayer is from about 1 to about 8 microns thick and consists essentially of cellulose acetate having from about 36.5 weight percent to about 40.0 weight percent acetyl content.

17. The electrode of claim 16 wherein said halide ions are chloride ions and said silver halide is silver chloride.

18. The electrode of claim 16 wherein said halide ion-permeable overlayer contains a surfactant.

19. A method for determining halide ion concentration in an aqueous solution, said method comprising the steps of:
  (a) bringing a portion of said aqueous solution into contact with a halide ion-permeable overlayer superposed on a layer of silver halide which is in electrochemical contact with means for making potentiometric measurements related to halide ion concentration, said halide ion-permeable overlayer consisting essentially of a composition: (1) being from about 1 to about 8 microns thick; (2) having a diffusion coefficient of at least $2.5 \times 10^{-10}$ cm$^2$/sec with respect to the halide ions whose concentration is to be determined; and (3) having a permeability of less than $2 \times 10^{-8}$ cm$^2$/sec to materials which could interfere with said determination of halide ion concentration; and
  (b) measuring the difference in potential between said portion of aqueous solution and said silver halide layer within 5 minutes after said portion of aqueous solution is brought into contact with said halide ion-permeable overlayer.

20. The method of claim 19 wherein said halide ion concentration is chloride ion concentration and said silver halide is silver chloride.

21. The method of claim 19 wherein said halide ion-permeable overlayer contains a surfactant.

22. The method of claim 19 wherein said means for making potentiometric measurements comprises a doped silicon support having a silicon dioxide layer superposed thereon.

23. A method for determining halide ion concentration in an aqueous solution, said method comprising the steps of:
  (a) bringing a portion of said aqueous solution into contact with a halide ion-permeable overlayer superposed on a layer of silver halide which is in electrochemical contact with means for making potentiometric measurements related to halide ion concentration, said halide ion-permeable overlayer being from about 1 to about 8 microns thick and consisting essentially of a composition selected from the group consisting of:
    (1) cellulose esters having from about 36.5 weight percent to about 40.0 weight percent acetyl content;
    (2) polymers derived from 45 weight percent to 100 weight percent of one or a mixture of monomers selected from the group consisting of:
      (i) acrylic acids;
      (ii) methacrylic acids;
      (iii) acrylamides;
      (iv) alkylacrylamides wherein the alkyl portion has from 1 to 5 carbon atoms;
      (v) hyroxyalkyl acrylates wherein the alkyl portion has from 1 to 5 carbon atoms; and
      (vi) hydroxyalkyl methacrylates wherein the alkyl portion has from 1 to 5 carbon atoms; and
    (3) mixtures of gelatin, silver halide/gelatin emulsion and an acid; and
  (b) measuring the difference in potential between said portion of aqueous solution and said silver halide layer after said portion of aqueous solution is brought into contact with said halide ion-permeable overlayer.

24. The method of claim 23 wherein said halide ion-permeable overlayer consists essentially of a composition selected from the group consisting of:
  (a) cellulose acetate having from about 36.5 weight percent to about 40.0 weight percent acetyl content;
  (b) poly(acrylamide-co-methacrylic acid) (weight ratio: 45/55);
  (c) poly(methacrylamide-co-methacrylic acid) (weight ratio: 50/50);
  (d) poly(methacrylamide-co-2-hydroxyethylmethacrylate-co-methacrylic acid-co-2-acetoacetoxyethylmethacrylate) (weight ratio: 28/28/34/10);
  (e) poly(methacrylic acid);
  (f) poly(acrylic acid); and
  (g) poly(2-hydroxyethylacrylate).

25. A method for determining halide ion concentration in an aqueous solution, said method comprising the steps of:

(a) bringing a portion of said aqueous solution into contact with a halide ion-permeable overlayer superposed on a layer of silver halide which is in electrochemical contact with means for making potentiometric measurements related to halide ion concentration, said halide ion-permeable overlayer being from about 1 to about 8 microns thick and consisting essentially of cellulose acetate having from about 36.5 weight percent to about 40.0 weight percent acetyl content; and (b) measuring the difference in potential between said portion of aqueous solution and said silver halide layer within 5 minutes after said portion of aqueous solution is brought into contact with said halide ion-permeable overlayer.

26. The method of claim 25 wherein said halide ion concentration is chloride ion concentration and said silver halide is silver chloride.

27. The method of claim 25 wherein said halide ion-permeable overlayer contains a surfactant.

28. The method of claim 25 wherein said means for making potentionmetric measurements comprises a doped silicon support having a silicon dioxide layer superposed thereon.

29. A method for determining halide ion concentration in an aqueous solution, said method comprising the steps of:

(a) bringing a portion of said aqueous solution into contact with a halide ion-permeable overlayer superposed on a layer of silver halide which is superposed on and in electrochemical contact with a layer of silver, said halide ion-permeable overlayer consisting essentially of a composition: (1) being from about 1 to about 8 microns thick; (2) having a diffusion coefficient of at least $2.5 \times 10^{-10}$ cm$^2$/sec with respect to the halide ions whose concentration is to be determined; and (3) having a permeability of less than $2 \times 10^{-8}$ cm$^2$/sec to materials which could interfere with said determination of halide ion concentration; and (b) measuring the difference in potential between said portion of aqueous solution and said silver halide layer within 5 minutes after said portion of aqueous solution is brought into contact with said halide ion-permeable overlayer.

30. The method of claim 29 wherein said halide ion concentration is chloride ion concentration and said silver halide is silver chloride.

31. The method of claim 29 wherein said halide ion-permeable overlayer contains a surfactant.

32. A method for determining halide ion concentration in an aqueous solution, said method comprising the steps of:

(a) bringing a portion of said aqueous solution into contact with a halide ion-permeable overlayer superposed on a layer of silver halide which is superposed on and in electrochemical contact with a layer of silver, said halide ion-permeable overlayer being from about 1 to about 8 microns thick and consisting essentially of a composition selected from the group consisting of:
(1) cellulose esters having from about 36.5 weight percent to about 40.0 weight percent acetyl content;
(2) polymers derived from 45 weight percent to 100 weight percent of one or a mixture of monomers selected from the group consisting of:
(i) acrylic acids;
(ii) methacrylic acids;
(iii) acrylamides;
(iv) alkylacrylamides wherein the alkyl portion has from 1 to 5 carbon atoms;
(v) hydroxyalkyl acrylates wherein the alkyl portion has from 1 to 5 carbon atoms; and
(vi) hydroxyalkyl methacrylates wherein the alkyl portion has from 1 to 5 carbon atoms; and
(3) mixtures of gelatin, silver halide/gelatin emulsion and an acid; and (b) measuring the difference in potential between said portion of aqueous solution and said silver halide layer after said portion of aqueous solution is brought into contact with said halide ion-permeable overlayer.

33. The method of claim 32 wherein said halide ion-permeable overlayer consists essentially of a composition selected from the group consisting of:
(a) cellulose acetate having from about 36.5 weight percent to 40.0 weight percent acetyl content;
(b) poly(acrylamide-co-methacrylic acid) (weight ratio: 45/55);
(c) poly(methacrylamide-co-methacrylic acid) (weight ratio: 50/50);
(d) poly(methacrylamide-co-2-hydroxyethylmethacrylate-co-methacrylic acid-co-2-acetoacetoxyethylmethacrylate) (weight ratio: 28/28/34/10);
(e) poly(methacrylic acid);
(f) poly(acrylic acid); and
(g) poly(2-hydroxyethylacrylate).

34. A method for determining halide ion concentration in an aqueous solution, said method comprising the steps of:

(a) bringing a portion of said aqueous solution into contact with a halide ion-permeable overlayer superposed on a layer of silver halide which is superposed on and in electrochemical contact with a layer of silver, said halide ion-permeable overlayer being from about 1 to about 8 microns thick and consisting essentially of cellulose acetate having from about 36.5 weight percent to about 40.0 weight percent acetyl content; and (b) measuring the difference in potential between said portion of aqueous solution and said silver halide layer within 5 minutes after said portion of aqueous solution is brought into contact with said halide ion-permeable overlayer.

35. The method of claim 34 wherein said halide ion concentration is chloride ion concentration and said silver halide is silver chloride.

36. The method of claim 34 wherein said halide ion-permeable overlayer contains a surfactant.

37. A method of inhibiting interference in a halide ion concentration determination, said method comprising the steps of:

(a) bringing a portion of said aqueous solution into contact with a halide ion-permeable overlayer superposed on a layer of silver halide which is in electrochemical contact with means for making potentiometric measurements related to halide ion concentration, said halide ion-permeable overlayer consisting essentially of a composition: (1) being from about 1 to about 8 microns thick; (2) having a diffusion coefficient of at least $2.5 \times 10^{-10}$ cm$^2$/sec with respect to the halide ions whose concentration is to be determined; and (3) having a permeability of less than $2 \times 10^{-8}$ cm$^2$/sec to materials which could interfere with said determination of halide ion concentration; and (b) measuring the difference in potential between said portion of aqueous solution and said silver halide layer within 5 minutes after said portion of aqueous solution is brought into contact with said halide ion-permeable overlayer.

38. A method of inhibiting interference in a halide ion concentration determination, said method comprising the steps of:
(a) bringing a portion of said aqueous solution into contact with a halide ion-permeable overlayer superposed on a layer of silver halide which is in electrochemical contact with means for making potentiometric measurements related to halide ion concentration, said halide ion-permeable overlayer being from about 1 to about 8 microns thick and consisting essentially of a composition selected from the group consisting of:
(1) cellulose esters having from about 36.5 weight percent to about 40.0 weight percent acetyl content;
(2) polymers derived from 45 weight percent to 100 weight percent of one or a mixture of monomers selected from the group consisting of:
(i) acrylic acids;
(ii) methacrylic acids;
(iii) acrylamides;
(iv) alkylacrylamides wherein the alkyl portion has from 1 to 5 carbon atoms;
(v) hydroxyalkyl acrylates wherein the alkyl portion has from 1 to 5 carbon atoms; and
(vi) hydroxyalkyl methacrylates wherein the alkyl portion has from 1 to 5 carbon atoms; and
(3) mixtures of gelatin, silver halide/gelatin emulsion and an acid; and
(b) measuring the difference in potential between said portion of aqueous solution and said silver halide layer after said portion of aqueous solution is brought into contact with said halide ion-permeable overlayer.

39. The method of claim 38 wherein said halide ion-permeable overlayer consists essentially of a composition selected from the group consisting of:
(a) cellulose acetate having from about 36.5 weight percent to about 40.0 weight percent acetyl content;
(b) poly(acrylamide-co-methacrylic acid) (weight ratio: 45/55);
(c) poly(methacrylamide-co-methacrylic acid) (weight ratio: 50/50);
(d) poly(methacrylamide-co-2-hydroxyethylmethacrylate-co-methacrylic acid-co-2-acetoacetoxyethylmethacrylate) (weight ratio: 28/28/34/10);
(e) poly(methacrylic acid);
(f) poly(acrylic acid); and
(g) poly(2-hydroxyethylacrylate).

* * * * *